United States Patent
Van Der Meulen et al.

(10) Patent No.: US 8,834,633 B2
(45) Date of Patent: Sep. 16, 2014

(54) PRE-TREATMENT OF CELLULOSIC MATERIAL

(75) Inventors: Torbjörn Van Der Meulen, Örnsköldsvik (SE); Stanley Forss, Bjästa (SE); Lars Elfving, Sidensjö (SE); Staffan Magnusson, Örnsköldsvik (SE); Magnus Hägglund, Domsjö (SE); Anders Sjöblom, Bonässund (SE)

(73) Assignee: Sekab E-Technology AB (SE)

( * ) Notice: Subject to any disclaimer, the term of this patent is extended or adjusted under 35 U.S.C. 154(b) by 63 days.

(21) Appl. No.: 13/517,288

(22) PCT Filed: Dec. 17, 2010

(86) PCT No.: PCT/EP2010/070134
§ 371 (c)(1),
(2), (4) Date: Feb. 20, 2013

(87) PCT Pub. No.: WO2011/080131
PCT Pub. Date: Jul. 7, 2011

(65) Prior Publication Data
US 2013/0143289 A1    Jun. 6, 2013

(30) Foreign Application Priority Data
Dec. 21, 2009    (EP) ..................................... 09180192

(51) Int. Cl.
*C13K 13/00*    (2006.01)
*C12P 7/10*    (2006.01)
(Continued)

(52) U.S. Cl.
CPC . *C13K 13/00* (2013.01); *C12P 7/10* (2013.01); *C12M 45/06* (2013.01); *Y02E 50/343* (2013.01); *D21C 3/02* (2013.01); *C12M 45/09* (2013.01); *C12P 7/16* (2013.01); *Y02E 50/10* (2013.01); *D21C 1/10* (2013.01); *C12P 2201/00* (2013.01); *D21C 3/06* (2013.01); *C12P 7/46* (2013.01); *C12P 2203/00* (2013.01); *Y02E 50/16* (2013.01); *C12M 21/12* (2013.01)
USPC ........ 127/1; 127/37; 162/52; 162/63; 162/83; 162/246; 162/250; 198/657

(58) Field of Classification Search
CPC .......... B01D 3/001; B30B 9/14; B65G 33/08; C12P 7/10; C12P 19/14; C12P 7/16; C12P 7/46; C12P 2201/00; C12P 2203/00; C13K 13/00; D21C 1/00; D21C 1/10; D21C 3/02; D21C 3/06; D21C 7/00; D21C 7/06; D21C 7/10; C12M 21/12; C12M 45/06; C12M 45/09; Y02E 50/10; Y02E 50/16; Y02E 50/343
USPC .............. 127/1, 37; 162/52, 63, 83, 246, 250; 198/657
See application file for complete search history.

(56) References Cited

U.S. PATENT DOCUMENTS

| | | |
|---|---|---|
| 4,995,943 A | 2/1991 | Rehberg |
| 2004/0060673 A1 | 4/2004 | Phillips et al. |

FOREIGN PATENT DOCUMENTS

| | | | |
|---|---|---|---|
| EP | 0 105 937 A1 | | 4/1984 |
| EP | 0105937 A1 | * | 4/1984 |

(Continued)

OTHER PUBLICATIONS

The Written Opinion of the International Searching Authority for PCT/EP2010/070134, dated Mar. 8, 2011.*

(Continued)

*Primary Examiner* — David A Reifsnyder
(74) *Attorney, Agent, or Firm* — Myers Bigel Sibley & Sajovec, P.A.

(57) ABSTRACT

A method of pre-treating a cellulosic material before hydrolysis is provided. The method comprises the steps of: impregnating the cellulosic material with a reactive water-soluble gas, such as sulphur dioxide ($SO_2$) or carbon dioxide ($CO_2$), in an impregnation chamber to obtain impregnated material; and heating the impregnated material to obtain pre-treated material, wherein the cellulosic material is compressed right before or when it is transferred to the impregnation chamber. A corresponding system is also provided.

16 Claims, 3 Drawing Sheets

(51) Int. Cl.
*C12P 7/16* (2006.01)
*C12P 7/46* (2006.01)
*D21C 1/10* (2006.01)
*D21C 3/02* (2006.01)
*D21C 3/06* (2006.01)
*C12M 1/00* (2006.01)

(56) References Cited

FOREIGN PATENT DOCUMENTS

| | | | |
|---|---|---|---|
| GB | 549 551 A | 11/1942 |
| GB | 910 002 A | 11/1962 |
| GB | 916 867 A | 1/1963 |
| GB | 974 341 A | 11/1964 |
| WO | WO 87/01402 A1 | 3/1987 |
| WO | WO 00/52256 A1 | 9/2000 |
| WO | WO 03/071025 A2 | 8/2003 |
| WO | WO 2008/144903 A1 | 12/2008 |
| WO | WO 2010/022511 A1 | 3/2010 |

OTHER PUBLICATIONS

International Preliminary Report on Patentability Corresponding to International Application No. PCT/EP2010/070134; Date of Mailing: May 11, 2012; 8 Pages.

International Search Report Corresponding to International Application No. PCT/EP2010/070134; Date of Mailing: Aug. 3, 2011; 5 Pages.

Öhgren, K. et al., "Optimization of Steam Pretreatment of $SO_2$—Impregnated Corn Stover for Fuel Ethanol Production", *Applied Biochemistry and Biotechnology*, vol. 121-124, 2005, pp. 1055-1068.

Puri, V.P. et al., "Explosive Pretreatment of Lignocellulosic Residues with High-Pressure Carbon Dioxide for the Production of Fermentation Substrates", *Biotechnology and Bioengineering*, vol. 25, No. 12, Dec. 1983, pp. 3149-3161.

CN 201080058066.6: filed Dec. 17, 2010; office action mailed Jun. 27, 2013.

* cited by examiner

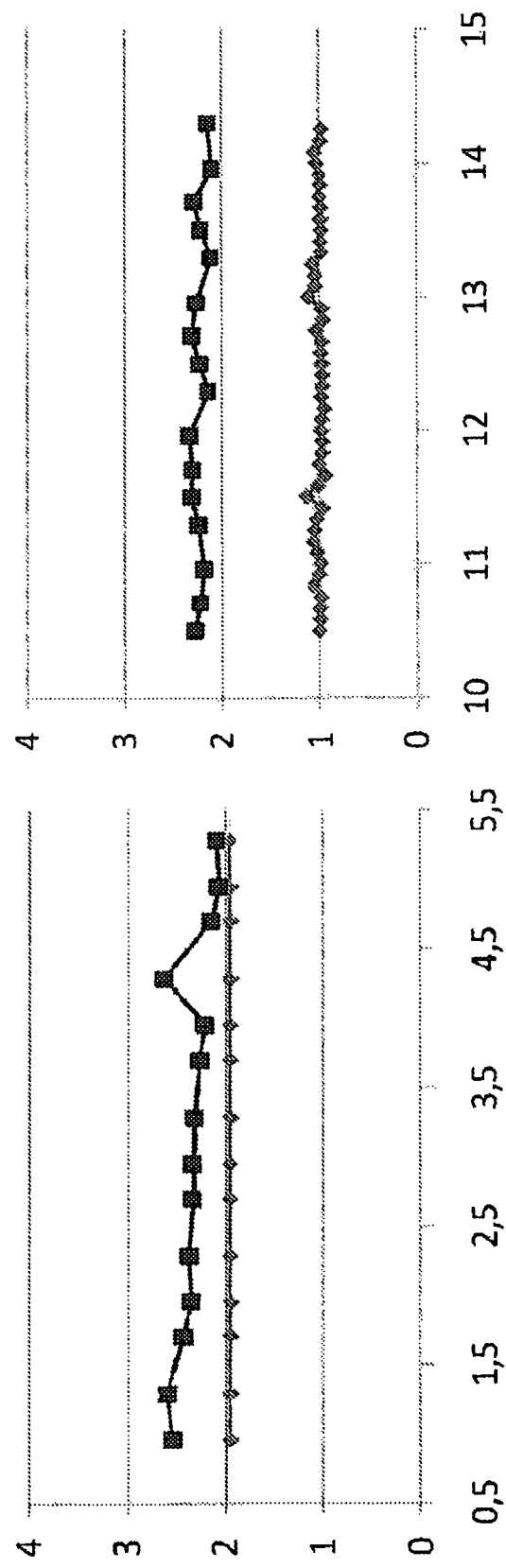

PRE-TREATMENT OF CELLULOSIC MATERIAL

RELATED APPLICATIONS

This application is a 35 U.S.C. §371 national phase application of PCT Application PCT/EP2010/070134, filed Dec. 17, 2010, which claims priority to EP 09180192.8, filed Dec. 21, 2009. The entire content of each of these applications is incorporated herein by reference.

FIELD OF THE PRESENT DISCLOSURE

The present disclosure relates to the field of preparation of a target chemical from cellulosic material.

BACKGROUND

A number of chemicals (e.g. ethanol, butanol and succinic acid) can be made from cellulosic material in a process which involves hydrolysis of the cellulosic material to obtain mono- and di-saccharaides followed by biological conversion of the saccharides to the target chemical.

In the hydrolysis step, enzymes or mineral acids may be employed for hydrolysing the polysaccharides of the cellulose. In order for such polysaccharides to become more accessible to the hydrolytic agents, the cellulosic material may be pre-treated. Pre-treatment is particularly important when the cellulosic material is lignocellulosic material, because the lignin of the lignocellulose protects the cellulosic polysaccharides from the hydrolytic activity.

Various pre-treatments have been described in the prior art. Steam explosion, wet oxidation and ammonia fiber explosion (AFEX pre-treatment) are some proposed variants. Alkali treatment is another (see e.g. WO09025547 and U.S. Pat. No. 5,693,296 A). A number of pre-treatments based on milder acidic conditions have also been suggested.

Further, different methods based on mechanical treatment of the cellulosic material have been described.

SUMMARY OF THE PRESENT DISCLOSURE

The inventors have realized that impregnation with a water soluble gas, which is reactive in itself or when dissolved in water, followed by heating is a promising method for pre-treatment of cellulosic material, such as wooden chips and bagass. The inventors have however noted that it has been difficult to control and predict the result of such a pre-treatment. The inventors conclude that the degree of impregnation has been varying from time to time.

It is thus an object of the present disclosure to provide for controllability in pre-treatment of cellulosic material.

The following is an itemized listing of embodiments, presented for the purpose of providing various aspects, features and combinations of the present disclosure.

BRIEF DESCRIPTION OF THE FIGURES

FIG. 3 shows the amount of $SO_2$ (g) (kg/h) (♦) added in pre-treatment of wooden chips and the pH (■) of the resulting slurry before (FIG. 3A) and after (FIG. 3B) a plug screw feeder was used for transferring the wooden chips to the impregnation chamber. The data represents five-day periods of continuous pre-treatment (the x-axis shows days).

DETAILED DESCRIPTION

Figure 1:
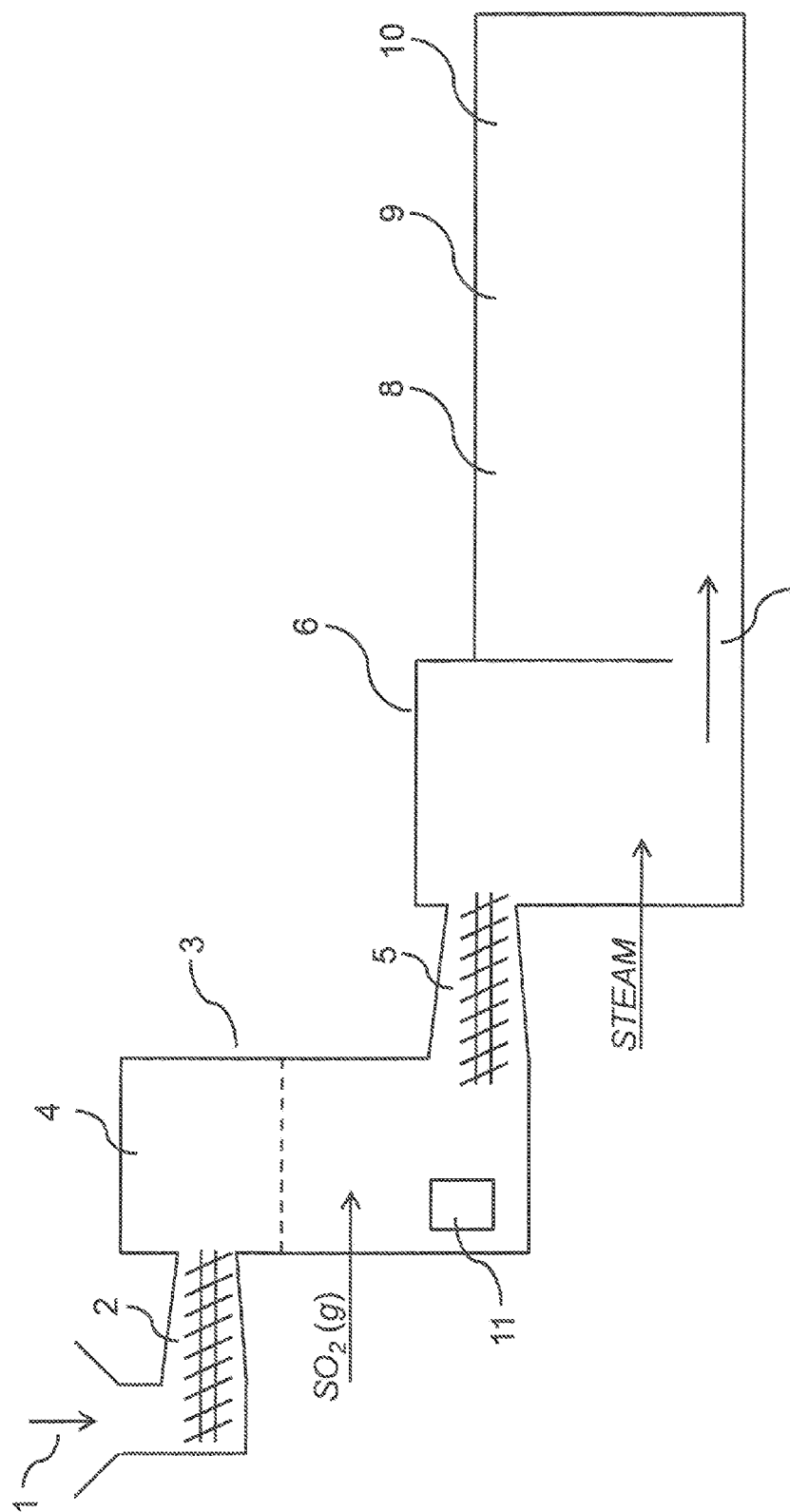
FIG. 1 shows a system for pretreating lignocellulosic material.

As a first aspect of the present disclosure, there is thus provided a method of pre-treating a cellulosic material before hydrolysis, comprising the steps of:

a) impregnating the cellulosic material with a reactive water-soluble gas, such as sulphur dioxide ($SO_2$) or carbon dioxide ($CO_2$), in an impregnation chamber to obtain impregnated material; and b) heating the impregnated material to obtain pre-treated material, wherein the cellulosic material is compressed when transferred to the impregnation chamber.

The inventors have realized that compressing the cellulosic material during its transfer to the impregnation chamber results in a more efficient impregnation as compared to transferring the cellulosic material without compression.

Without being bound to any specific scientific theory, the inventors believe that the compression serves to control the dry matter content of the cellulosic material to be impregnated. That is, while the dry matter contents of the cellulosic raw material may vary to a substantial degree over time (for example from one season to another), the dry matter contents of the compressed material will vary less. In particular, the inventors believe that the compression reduces the amount of moist present on the surface of the cellulosic material. This is believed to be beneficial since gaseous $SO_2$ and $CO_2$ are highly soluble in water and surface moist may therefore prevent the gaseous $SO_2$ or $CO_2$ from penetrating the cellulosic material (an efficient penetration is believe to one of the major causes of an efficient impregnation).

Also, the compression may increase the specific surface area of the cellulosic material by "crushing" it. This may also facilitate the impregnation. In particular, the specific surface area of relatively dry cellulosic material, such as corn cobs, may be significantly increased during the compression.

Further and again without being bound to any specific scientific theory, since the compressed material in most cases will expand when entering the impregnation chamber, the reactive water-soluble gas (such as $SO_2$ or $CO_2$) in the impregnation chamber is believed to be "sucked" into the expanding material to some extent. In other words, the expansion may provide for an efficient penetration.

The beneficial effect of the compression on the results of impregnations is shown below under Examples.

In addition to the improved predictability, the present disclosure may also provide for lower consumption of the reactive water-soluble gas.

In an alternative manner, the cellulosic material may be compressed right before it is transferred to the impregnation chamber, which means that no step of processing the cellulosic material is performed between the compression and the transfer to the impregnation chamber.

In embodiments of the first aspect of the present disclosure, the cellulosic material may thus be compressed to such a degree that it expands when entering the impregnation chamber and/or its dry matter content increases.

Also, in embodiments of the first aspect of the present disclosure, the cellulosic material may be subjected to a pressure of at least 5 bar, such as at least 10 bar, such as at least 30 bar during the compression.

Further, in alternative or complementing embodiments of the first aspect of the present disclosure, the bulk density of the cellulosic material is increased with at least 20%, such as at least 40%, such as at least 60%, such as at least 80%, such as at least 100%. The bulk density increase may vary considerably between different cellulosic materials and may for example depend of the shape of the individual pieces of the cellulosic material before the compression.

The "dry matter content" is the ratio between the weight of the material when completely dried and the weight of the material. Frequently, dry matter content is expressed as weight percentage (w. %). The "dry matter content" of a material is thus a measure of the amount of non-water components in the material.

As explained above, the dry matter content of the cellulosic material may be increased during the compression. In embodiments of the first aspect, the cellulosic material may be compressed to such an extent that the dry matter content is increased by at least 5%, such as at least 8%. Here, the dry matter content (DM) increase is calculated as $(DM_{after\ compression} - DM_{before\ compression})/DM_{before\ compression}$. Many fresh lignocellulosic materials have a dry matter content of about 50%. Thus, if the DM is 50% before the compression and 55% after the compression, the increase is (55−50)/50=10%. Normally, cellulosic materials of lower dry matter contents are dewatered to a larger extent during the compression than cellulosic materials of higher dry matter contents.

The dry matter content of the cellulosic material may also be used for controlling the compression. In embodiments of the first aspect of the present disclosure, the dry matter content of cellulosic material may thus be measured and the degree of compression of the cellulosic material transferred to the impregnation chamber may be adapted in response to the measured dry matter content. Even though it is possible to measure the dry matter contents of the cellulosic material before the compression, the measurement is preferably performed on cellulosic material that has been compressed, such as cellulosic material in the impregnation chamber.

The degree of compression may for example be increased if the measured dry matter content is below a first reference value and decreased if the measured dry matter content is above a second reference value.

The above-mentioned measurement and adaptation of compression may provide for more stable properties of the material to be impregnated and thereby a more predictable result of the impregnation.

The transfer and compression of the first aspect may for example be achieved by means of a plug screw feeder. Plug screw feeders are discussed in more detail below.

When using a plug screw feeder, the degree of compression may be adapted by adjusting the speed of the plug screw feeder; the lower the speed, the higher the compression rate.

Also, the plug screw feeder may comprise an abutment which is arranged to split up the plug of compressed material leaving the plug screw feeder. The abutment, which normally is adjustable, applies a pressure on the plug. The degree of compression may thus be adapted by adjusting the pressure applied by the abutment; the higher the applied pressure, the higher the compression rate. To facilitate this, the part of the abutment that is contacted with the plug may be arranged on a piston.

To facilitate the splitting-up of the plug, the abutment may comprise a point aimed towards the plug. The design of the point may be adapted to a given cellulosic material.

Examples of plug screw feeders which may be employed in the context of the present disclosure are disclosed in U.S. Pat. No. 5,996,770 and WO 91/04371. Further, plug screw feeders are available from Andritz (e.g. the Impressafiner) and Metso.

In the context of the present disclosure, a "reactive water-soluble gas" refers to a gas which reacts with a cellulosic material, such as a lignocellulosic material, or dissolves in water to form a solution that reacts with the cellulosic material. In preferred embodiments, the reactive water-soluble gas is $CO_2$ or $SO_2$. In the case of $CO_2$, $SO_2$ or other weakly acidic gases, the water solution comprises reactive protons.

Impregnating the cellulosic material with a reactive water-soluble gas may be achieved by adding the reactive soluble gas to the impregnation chamber. This may thus provide for a controlled amount of gas being added to the cellulosic material. Further, the reactive water-soluble gas may further be present in the impregnation chamber already when the cellulosic material enters the impregnation chamber, which provides for a rapid and efficient impregnation of the cellulosic material in the impregnation chamber.

The method of the first aspect may be continuous, which means that, for a period of time, cellulosic material is continuously transferred to the impregnation chamber and impregnated material is continuously transferred to the heating. Further, pre-treated material may be continuously transferred from the heating.

In the context of the present disclosure, the pressures defined herein is the absolute pressure in the impregnation chamber. Thus, the pressures defined herein in bar is the absolute pressure. The unit bar could therefore also be expressed as "bara".

The inventors have shown that an efficient impregnation may be achieved without increasing the pressure in the impregnation chamber.

In embodiments of the first aspect of the present disclosure, the pressure in the impregnation chamber may thus be 0.5-15 bar, such as 0.5-10 bar, such as 0.5-5.0 bar, such as 0.7-3.0 bar, such as 0.8-1.5 bar As other examples, the pressure in the impregnation chamber may be 1.0-5.0 bar, such as 1.0-3.0 bar, such as 1.0-1.5 bar. The inventors have further realized that higher temperatures may impair impregnation efficiency, in particular in the case of $SO_2$ impregnation, which probably is due to the volatility of $SO_2$ (g). In embodiments of the first aspect of the present disclosure, the temperature of the impregnation may thus be 5-120° C., such as 5-95° C.

In the Examples below, $SO_2$ impregnations are shown to give a satisfactory result. The inventors believe that even though $SO_2$ impregnations may be the most efficient, impregnations with other weakly acidic gases, such as $CO_2$, are also likely to work. In a preferred embodiment of the present disclosure, the cellulosic material is thus impregnated with $SO_2$. In embodiments, the cellulosic material is impregnated with $CO_2$. There are however some benefits to using $CO_2$. Firstly, $CO_2$ is free from sulphur, which is beneficial from an environmental perspective. Secondly, the $CO_2$ may be obtained from a fermentation of hydrolyzed material downstream of the pre-treatment. $CO_2$ is for example produced when sugars are fermented to ethanol using yeast as the fermenting agent.

In embodiments of the first aspect, the pressure in the impregnation chamber is 0.5-15 bar, such as 0.5-10 bar, such as 0.5-5.0 bar, such as 0.7-3.0 bar, such as 0.8-1.5 bar when $CO_2$ is employed. The inventors have found that pressures within these ranges give satisfactory results when using $CO_2$.

In the Examples below, the $SO_2$ is added in the form of a gas. Further, most of the $SO_2$ in the impregnation chamber is in gaseous form.

In embodiments of the first aspect, the pressure in the impregnation chamber is 0.5-10 bar, such as such as 0.5-5.0 bar, such as 0.7-3.0 bar, such as 0.8-1.5 bar when $SO_2$ is employed. The inventors have found that pressures within these ranges give satisfactory results when using $SO_2$.

In embodiments of the first aspect, 0.1-10% (w/w) $SO_2$ is added per added dry matter of cellulosic material. Consequently, when 100 kg of cellulosic material, calculated as dry matter, is transferred to the impregnation chamber, 0.1-10 kg of $SO_2$ may be added to the same. In some embodiments, 0.25-2% (w/w) $SO_2$ is added per added dry matter of cellulosic material.

The "cellulosic material" of the present disclosure may be any material comprising cellulose. Examples of such materials are municipal paper waste, wood material, agricultural residues and energy crops. The wood material may be forestry residues, such as wood chips, sawmill or paper mill discards The municipal paper waste may be recycled paper or paperboard. As examples, the cellulosic material may comprise agricultural lignocellulose materials e.g. straw or corn residues (stover, cobs). Agricultural residues may also be corn stover, corn fiber, corn cobs, wheat straw, sugarcane bagasse, beet pulp, rice straw or soybean stover, and energy crops may be fast growing trees or woody grasses.

When handling lignocellulosic material, an efficient pre-treatment is particularly important because the cellulose and hemicellulose fibers of the native lignocellulose material are tightly associated with lignin, which make them less accessible to hydrolysis.

According to a preferred embodiment, the "cellulosic material" of the present disclosure is thus "lignocellulosic material". The lignocellulosic material may be selected from wood material, agricultural residues and energy crops, which are discussed above.

In the Examples below, the inventors show the benefits of the method of the first aspect using wood chips as the starting material. The inventors have also practiced the method of the first aspect using sugarcane bagass as the starting material.

The heating of step b) is normally performed under pressure, such as a pressure of 5-50 bar. The heating may be performed in one or more steps. The heating is normally achieved by addition of pressurized steam.

The method of the first aspect normally forms part of a process for making a target chemical. Such a process may involve one or more of the following steps subsequent to the pre-treatment:

c) hydrolysing the pre-treated material to obtain a hydrolyzate;

d) fermenting the hydrolyzate to obtain a target chemical-containing fermentation broth;

e) separation of the target chemical to obtain a target chemical-containing fraction and a residual fraction;

f) anaerobic treatment of the residual fraction to obtain biogas and a waste water fraction.

In the hydrolysis, cellulose and optionally hemicellulose polysaccharides are degraded to shorter saccharides, normally monosaccharides and/or disaccharides. The hydrolysis of step c) may for example be enzymatic hydrolysis, wherein the catalytic action of one or more enzymes is employed. Alternatively, the hydrolysis of step c) may be acidic hydrolysis, wherein the polysaccharides are subjected to a lower pH, such as a pH of 1-3. Acidic hydrolysis is normally performed under elevated temperature and pressure. The acidic hydrolysis may be performed in one or more steps. The person skilled in the art may without undue burden adapt an enzymatic or acidic hydrolysis to a given industrial context.

In the case of enzymatic hydrolysis, the pre-treated material (which normally is in the form of a slurry) may be neutralized by the addition of a neutralization agent, such as a salt of a base (e.g. NaOH, $Ca(OH)_2$, $CaCO_3$) or ammonium hydroxide. The pre-treated material may for example be neutralized to reach a pH of 4-7. The primary purpose of the neutralization is to obtain a pH under which the enzymes perform well, or in the case of SSF, under which the enzymes and the fermenting agents perform well (see explanation of SSF below). Different enzymes and fermenting agents may have different pH optima. Further, the temperature of the pre-treated material may be adjusted before the hydrolysis or SSF.

In the fermentation, the shorter saccharides are converted to the target chemical by one or more fermentation agents, such as yeast and/or bacterium. For example, the fermentation agents may comprise a first agent capable of converting hexoses to the target chemical and a second agent capable of converting pentoses to the target chemical. Also, the same fermentation agent may be capable of converting both pentoses and hexoses to the target chemical.

If the hydrolysis is enzymatic, the hydrolysis and fermentation may be performed simultaneously, e.g. in the same vessel. Such a process is sometimes referred to as "Simultaneous Saccharification and Fermentation" (SSF). The person skilled in the art may without undue burden adapt a fermentation or an SSF to a given industrial context.

A solid residue comprising lignin may be obtained from any one of steps b)-f). This can be a valuable product that may be used as fuel, for example in production of heat or electricity.

The target chemical of the present disclosure may be any chemical that can be produced from shorter saccharides by fermenting agents. Examples of such chemicals are ethanol, butanol and succinic acid.

The method of the first aspect may thus represent some of the first steps in a method for making a target chemical, such as ethanol from cellulose. In the ethanol-making processes, the fermenting agents are normally yeasts. In the art, yeasts capable of converting hexoses and pentoses, respectively, have been described. The person skilled in the art is aware of different yeast strains that have been adapted to the conditions present in the process of making ethanol from cellulose. However, it is to be understood that the present disclosure is not limited to any specific yeast strain or fermentation method.

As a second aspect of the present disclosure, there is provided a system comprising an impregnation chamber for impregnating the cellulosic material with a reactive water-soluble gas (such as $SO_2$ or $CO_2$) connected to a heating unit for heating impregnated cellulosic material, wherein a plug screw feeder for feeding the cellulosic material to the impregnation chamber is arranged at the impregnation chamber. The system is primarily intended to be part of a plant for production of a target chemical, such as ethanol, from a cellulosic material.

The embodiments of the first aspect described above apply mutatis mutandis to the second aspect. Further, the benefits of the second aspect follow from the above discussion about the method of the first aspect and the embodiments thereof.

Some non-limiting embodiments of the second aspect are anyway described below.

In embodiments of the second aspect, the impregnation chamber may comprise at least one inlet for the reactive water-soluble gas. The inlet(s) may for example be arranged above the bottom of the impregnation chamber. Such an arrangement is beneficial because water may be accumulated on the bottom of the impregnation chamber, and letting $SO_2$ or $CO_2$ gas pass a layer of water could reduce the amount of $SO_2$ or $CO_2$ available for the impregnation since the $SO_2$ or $CO_2$ gas is very soluble in water. (Of course, this also applies to other water-soluble gases). In some embodiments, the impregnation chamber may comprise at least two, such as at least three or four, inlets. A higher number of inlets may provide for more even distribution of the gas in the cellulosic material present in the impregnation chamber.

In embodiments of the second aspect, the impregnation chamber may have an upper half and a lower half and the plug screw feeder may be arranged at the upper half. By arranging the cellulosic material inlet (here, the plug screw feeder) at the upper half of the impregnation chamber, the gravity force may be utilized for moving the cellulosic material through the impregnation chamber. Transportation screws may also assist in this purpose.

Accordingly, the impregnation chamber may comprise an outlet for impregnated cellulosic material which is arranged at the lower half (e.g. near the bottom) of the impregnation chamber. Such an outlet is then connected to the heating unit.

In embodiments of the second aspect, a second plug screw feeder for transferring impregnated cellulosic material from the impregnation chamber to the heating unit may be arranged in the connection between the impregnation chamber and the heating unit. Consequently, such a plug screw feeder may be connected to the outlet of the impregnation chamber.

The heating is normally performed under over pressure, and a plug screw feeder is an efficient alternative for moving material from a zone of lower pressure to a zone of higher pressure. Note that this is not the reason for using a plug screw feeder to transfer the cellulosic material to the impregnation chamber.

In some embodiments, more than one heating unit may be included in the system. In the art, the heating units are sometimes referred to as reactors.

In embodiments, the plant or system of the second aspect may further comprise one or more of the following units (arranged downstream of the heating unit):

a hydrolysis unit connected to the heating unit for hydrolysis of the pre-treated material from the heating unit;

a fermenting unit connected to the hydrolysis unit for fermenting hydrolyzate from the hydrolysis unit, a separation unit connected to the fermenting unit for separation of a target chemical from fermentation broth from the fermenting unit;

an anaerobic treatment unit connected to the separation unit for production of biogas from a residual fraction from the separation unit.

The hydrolysis unit may for example be adapted for enzymatic hydrolysis and in such case, a neutralization unit may be arranged in the connection between the heating unit and the hydrolysis unit. The neutralization unit may for example be a vessel in which the pre-treated material may be mixed with a neutralization agent, such as a salt of a base.

Further, if the hydrolysis unit is adapted for enzymatic hydrolysis, the hydrolysis unit and the fermenting unit may be the same apparatus. In such case, the apparatus is adapted for SSF.

Various embodiments of fermenting units, or "fermentors", are available. A fermentor may be adapted to SSF.

The separation unit may for example be a distillation unit. Distillation is a frequently used technique for separating ethanol from fermentation broth.

In embodiments, the plant or system of the second aspect may comprise a device for measuring a dry matter content of the cellulosic material, which generates a signal on the basis of the dry matter content measurement and applies the generated signal to the plug screw feeder, wherein said plug screw feeder responds to the applied signal by adapting the degree of compression of the cellulosic material in the plug screw feeder. Normally, the degree of compression is increased in response to a signal indicating a low dry matter content and decreased in response to a high dry matter content. "Adapting the degree of compression" may for example be adapting the speed of the plug screw feeder or adapting the pressure applied by the abutment, wherein a lower speed or a higher applied pressure results in a higher degree of compression. Other control mechanisms are discussed above in connection with the first aspect.

The device may for example comprise a radiation generator and a radiation detector for the dry matter content measurement. The radiation generator may for example be a microwave generator and the detector a microwave detector. Alternatively, or as a complement, the radiation generator may be an Infra Red (IR) generator and the detector may be an IR detector.

The device may be arranged in the impregnation chamber such that the dry matter content of the cellulosic material leaving the plug screw feeder (i.e. the cellulosic material entering the impregnation chamber) may be measured.

EXAMPLES

A non-limiting example of a method and system for pre-treating lignocellulosic material is described with reference to FIG. 1. Lignocellulosic material, such as sugarcane bagass or wooden chips, is added 1 to a plug screw feeder 2 arranged at the top of an impregnation chamber 3. While the lignocellulosic material is transferred to the impregnation chamber 3 in the plug screw feeder 2 it is compressed and thereby dewatered. At the outlet of the plug screw feeder 2, the compressed lignocellulosic material has the form of a plug which form a tight seal preventing leakage of $SO_2$ (g) out of the impregnation chamber 3. The upper part of the impregnation chamber 3 may comprise a mixing zone 4, in which the plug is broken up into smaller pieces to facilitate the impregnation. The mixing may be achieved by various techniques. For example, the plug screw feeder 2 may comprise an abutment arranged to split up the plug. $SO_2$ (g) is added to the impregnation chamber 3. The gas may for example be added though a plurality of inlets arranged above the bottom of the impregnation chamber. A second plug screw feeder 5 is arranged at the bottom of the impregnation chamber 3 for feeding impregnated material to a heating unit 6. The plug formed in the second plug screw feeder 5 allows for an increased pressure in the heating unit 6, in which pressurized steam is employed to complete the pre-treatment of the lignocellulosic material. The pre-treated lignocellulosic material is normally in the form of a slurry after the heat treatment in the heating unit 6. The slurry, which leaves the heating unit through an outlet 7, may then be hydrolyzed in the hydrolysis unit 8, fermented in the fermenting unit 9, and separated in the separation unit 10. If the hydrolysis is enzymatic, the slurry is normally neutralized before any contact with the enzymes. A device 11 for measuring the dry matter content of the cellulosic material may be arranged in the impregnation chamber 3.

Figure 2:
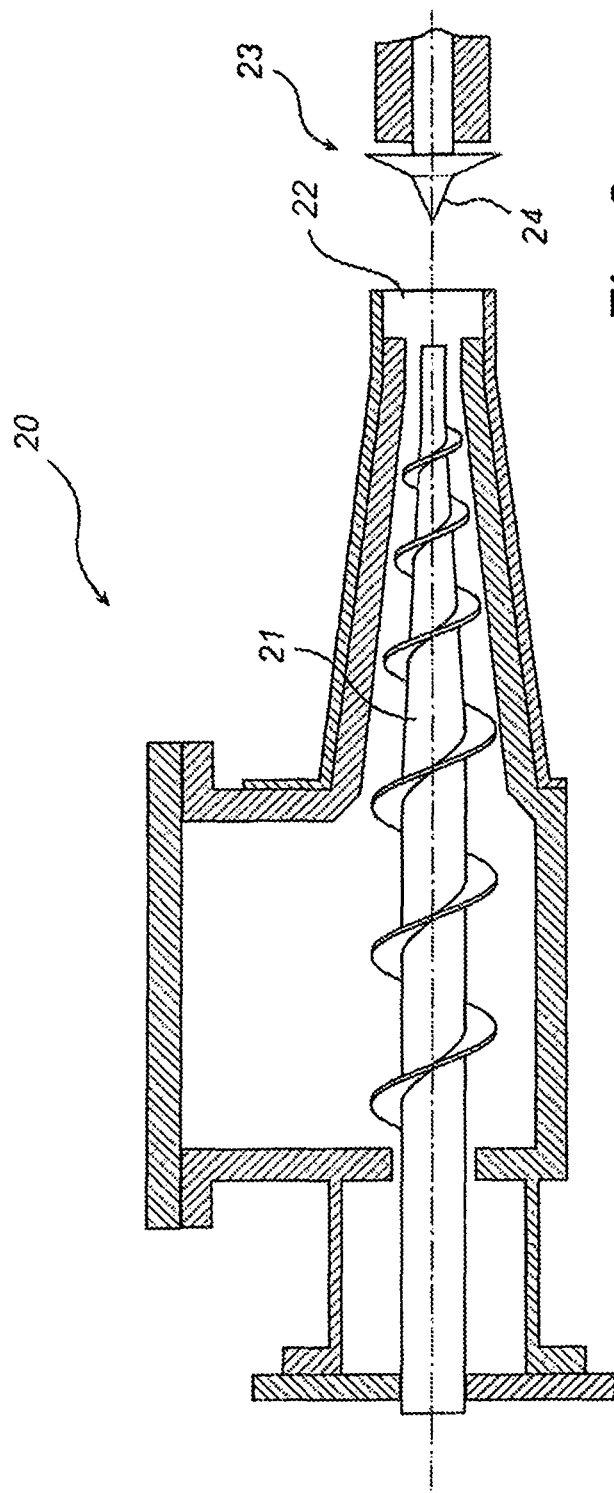
FIG. 2 is a simplified representation of a plug screw feeder which may be used in the context of the present disclosure.

A non-limiting example of a plug screw feeder is described with reference to FIG. 2. The plug screw feeder 20 comprises a screw 21 which, under operation, transfers and compresses material added to the plug screw feeder 20. Material added to the plug screw feeder 20 normally forms a compact plug in the outlet 22 of the plug screw feeder 20. The plug screw feeder 20 may further comprise an abutment 23 arranged to split up the plug as it leaves the outlet 22. The abutment 24 may comprise a pointy tip 24 to facilitate the splitting. The pressure applied by the abutment 23 on the plug may be adjustable.

Comparison of Pre-Treatment with and without Compression

In general, the inventors have noted that the pH of the liquid squeezed out of the impregnated material in the plug screw feeder 5 (see FIG. 1) and the pH of liquid from the pre-treated material/slurry became more stable when a plug screw feeder was employed for transferring wooden chips to the impregnation chamber.

FIG. 3 illustrate the effect of the plug screw feeder in continuous pre-treatment of wooden chips in SEKAB's pilot plant in Örnsköldsvik, Sweden.

In the trials behind FIG. 3, an impregnation chamber was connected to a first heating unit, which in turn was connected to a second heating unit. Wooden chips were fed to the impregnation chamber and a slurry (pre-treated material) was obtained from the second heating unit.

In the first part of the trials, 2 kg/h of $SO_2(g)$ was added to the impregnation chamber. A non-compacting transport screw was arranged for transferring the wooden chips to the impregnation chamber. The pressure in the impregnation chamber was approximately atmospheric. Further, steam was added to the first and second heating units such that the pressure was 6 bar in the first heating unit and 20 bar in the second heating unit. Wooden chips were continuously pre-treated over a five-day period and the pH of liquid from the slurry was measured. The resulting data is presented in FIG. 3A, which shows that the pH was varying to a substantial degree and that the pH was generally falling over the time period of the first part of the trials.

In the second part of the trials, about 1 kg/h of $SO_2$ (g) was added to the impregnation chamber. Further, a plug screw feeder was arranged for transferring the wooden chips to the impregnation chamber. The compression in the plug screw feeder resulted in dewatering of the wooden chips. Again the pressure in the impregnation chamber was approximately atmospheric. Steam was added to the first and second heating units. The pressure in the first heating unit was gradually increased from about 2 bar to about 6 bar during the five-day period of continuous pre-treatment. The pressure in the second heating unit was again 20 bar. pH of liquid from the slurry was measured and the resulting data is presented in FIG. 3B, which shows that the pH was varying to some degree. No general trend with regard to pH may however be observed.

If the results of FIG. 3A and 3B are compared, it may be concluded that the pH was more stable when the plug screw feeder was employed; the variations in FIG. 3B are smaller than in FIG. 3A, and FIG. 3B shows no general trend. Further, a supply of 1 kg/h of $SO_2$ (g) after the installation of the plug screw feeder resulted in about the same pH as a supply of 2 kg/h of $SO_2$ (g) before the installation. The plug screw feeder thus provided for lower $SO_2$ consumption. Further, the inventors believe that the first (low-pressure) heating step is of less importance and that it may be omitted. It is however notable that the pH remained stable in the second part of the trials even though the pressure in the first heating was changed.

The invention claimed is:

1. Plant for production of a target chemical from a cellulosic material, comprising:
    an impregnation chamber for impregnating the cellulosic material with sulphur dioxide ($SO_2$);
    a heating unit connected to the impregnation chamber for heating the impregnated cellulosic material,
    a hydrolysis unit connected to the heating unit for hydrolysis of the heated impregnated material from the heating unit thereby obtaining a hydrolyzate;
    a fermenting unit connected to the hydrolysis unit for fermenting the hydrolyzate from the hydrolysis unit thereby obtaining a fermentation broth containing the target chemical; and
    a separation unit connected to the fermenting unit for separation of the target chemical from the fermentation broth from the fermenting unit,
    wherein a plug screw feeder for feeding the cellulosic material to the impregnation chamber is arranged at the impregnation chamber and wherein the impregnation chamber comprises at least one inlet for the sulphur dioxide ($SO_2$).

2. Plant according to claim 1, wherein said at least one inlet is/are arranged above the bottom of the impregnation chamber.

3. Plant according to claim 1, wherein the impregnation chamber has an upper half and a lower half and the plug screw feeder is arranged at the upper half.

4. Plant according to claim 1, wherein the impregnation chamber comprises an outlet for impregnated cellulosic material which is arranged at the lower half of the impregnation chamber.

5. Plant according to claim 1, wherein the separation unit is a distillation unit.

6. Plant according to claim 1, further comprising a device for measuring a dry matter content of the cellulosic material, which device generates a signal on the basis of the dry matter content measurement and applies the generated signal to the plug screw feeder, said plug screw feeder responding to the applied signal by adapting the degree of compression of the cellulosic material in the plug screw feeder.

7. Plant according to claim 6, wherein said device is arranged in the impregnation chamber such that the dry matter content of cellulosic material leaving the plug screw feeder may be measured.

8. Plant according to claim 1, wherein the target chemical is selected from the group consisting of ethanol, butanol and succinic acid.

9. Plant for production of a target chemical from a cellulosic material, comprising:
    an impregnation chamber for impregnating the cellulosic material with sulphur dioxide ($SO_2$);
    a heating unit connected to the impregnation chamber for heating the impregnated cellulosic material;
    a hydrolysis and fermenting unit connected to the heating unit for hydrolysis and fermentation of the heated impregnated material from the heating unit thereby obtaining a fermentation broth containing the target chemical; and
    a separation unit connected to the hydrolysis and fermenting unit for separation of the target chemical from the fermentation broth from the hydrolysis and fermenting unit,
    wherein a plug screw feeder for feeding the cellulosic material to the impregnation chamber is arranged at the impregnation chamber and wherein the impregnation chamber comprises at least one inlet for the sulphur dioxide ($SO_2$).

10. Plant according to claim 9, wherein said at least one inlet is/are arranged above the bottom of the impregnation chamber.

11. Plant according to claim 9, wherein the impregnation chamber has an upper half and a lower half and the plug screw feeder is arranged at the upper half.

12. Plant according to claim 9, wherein the impregnation chamber comprises an outlet for impregnated cellulosic material which is arranged at the lower half of the impregnation chamber.

13. Plant according to claim 9, wherein the separation unit is a distillation unit.

14. Plant according to claim 9, further comprising a device for measuring a dry matter content of the cellulosic material, which device generates a signal on the basis of the dry matter content measurement and applies the generated signal to the plug screw feeder, said plug screw feeder responding to the applied signal by adapting the degree of compression of the cellulosic material in the plug screw feeder.

15. Plant according to claim 14, wherein said device is arranged in the impregnation chamber such that the dry matter content of cellulosic material leaving the plug screw feeder may be measured.

16. Plant according to claims 9, wherein the target chemical is selected from the group consisting of ethanol, butanol and succinic acid.

* * * * *